(12) United States Patent
Schmitt

(10) Patent No.: US 9,063,067 B1
(45) Date of Patent: Jun. 23, 2015

(54) MOISTURE SENSING DEVICES

(71) Applicant: Alvin P. Schmitt, Blacksburg, VA (US)

(72) Inventor: Alvin P. Schmitt, Blacksburg, VA (US)

(73) Assignee: Alvin P. Schmitt, Blacksburg, VA (US)

( * ) Notice: Subject to any disclaimer, the term of this patent is extended or adjusted under 35 U.S.C. 154(b) by 103 days.

(21) Appl. No.: 13/784,091

(22) Filed: Mar. 4, 2013

Related U.S. Application Data

(63) Continuation-in-part of application No. 13/292,504, filed on Nov. 9, 2011.

(60) Provisional application No. 61/414,657, filed on Nov. 17, 2010.

(51) Int. Cl.
| | | |
|---|---|---|
| *G01R 27/26* | (2006.01) | |
| *G01N 19/00* | (2006.01) | |
| *G01N 27/22* | (2006.01) | |
| *G01N 25/62* | (2006.01) | |
| *G08B 19/02* | (2006.01) | |

(Continued)

(52) U.S. Cl.
CPC .............. *G01N 27/223* (2013.01); *F21V 31/00* (2013.01); *G01N 27/225* (2013.01); *H05K 5/06* (2013.01)

(58) Field of Classification Search
CPC .... G01R 27/2605; G01R 27/26; G06F 3/044; G06F 17/30292; G01N 27/223; G01N 27/22; G06N 5/04; G06N 99/005; A61B 19/2203; A61B 2019/2223
USPC ........ 374/28, 16, 21; 324/658, 663–669, 679, 324/671, 688; 73/335.04, 335.08, 170.17, 73/170.26; 340/601–604, 962, 580; 318/483, 466
See application file for complete search history.

(56) References Cited

U.S. PATENT DOCUMENTS

| | | | |
|---|---|---|---|
| 2,043,241 | A | 6/1936 | Eyer |
| 2,076,441 | A | 4/1937 | Berry |

(Continued)

FOREIGN PATENT DOCUMENTS

| | | |
|---|---|---|
| AU | 241966 | 12/1960 |
| DE | 3900184 A1 | 8/1989 |
| GB | 2149922 A | 6/1985 |

OTHER PUBLICATIONS

US 6,552,552, 4/2003, Hirono et al. (withdrawn).

(Continued)

*Primary Examiner* — Vincent Q Nguyen
*Assistant Examiner* — Felicia Farrow
(74) *Attorney, Agent, or Firm* — New River Valley IP Law, PC; Michele L. Mayberry

(57) ABSTRACT

Capacitive moisture sensors for monitoring moisture conditions through the use of an electric field are provided, including sensing devices for determining the amount of moisture on a device and correlating this with an amount of moisture in the atmosphere to determine whether plants need more or less moisture. More specific embodiments of the invention provide a fringing capacitor sensor and a mesh cell sensor. Provided is a mesh cell sensor comprising: a first conductive electrode comprising a wire mesh array; a second conductive electrode disposed on a non-conductive support; an evaporative membrane disposed between the first and second electrodes; a box supporting the first and second electrodes and the evaporative membrane in a manner that provides for a hermetically sealed volume disposed between the evaporative membrane and the bottom of the box.

6 Claims, 9 Drawing Sheets

(51) Int. Cl.
  *F21V 31/00* (2006.01)
  *H05K 5/06* (2006.01)

(56) References Cited

U.S. PATENT DOCUMENTS

| | | | |
|---|---|---|---|
| 2,121,103 A | 6/1938 | Seeley |
| 2,207,906 A | 7/1940 | Weagant |
| 2,219,497 A | 10/1940 | Stevens et al. |
| 2,285,152 A | 6/1942 | Firestone |
| 2,357,984 A | 9/1944 | Charles |
| 2,373,846 A | 4/1945 | Hyman |
| 2,455,450 A | 12/1948 | Thompson |
| 2,508,081 A | 5/1950 | Kenyon Taylor et al. |
| 2,570,218 A | 10/1951 | Draganjac |
| 2,611,021 A | 9/1952 | Alfred Perls et al. |
| 2,662,408 A | 12/1953 | Ellison |
| 2,729,785 A | 1/1956 | Keevil |
| 2,817,234 A | 12/1957 | Campbell |
| 2,849,882 A | 9/1958 | Lee |
| 2,969,186 A | 1/1961 | Geiger |
| 3,046,479 A | 7/1962 | Mead et al. |
| 3,079,089 A | 2/1963 | Tomayer |
| 3,112,647 A | 12/1963 | Sontheimer |
| 3,129,415 A | 4/1964 | McKnight |
| 3,177,427 A | 4/1965 | Kuntz et al. |
| 3,218,551 A | 11/1965 | Cook |
| 3,231,815 A | 1/1966 | Spencer |
| 3,278,843 A | 10/1966 | Deming |
| 3,443,213 A | 5/1969 | Bader et al. |
| 3,515,987 A | 6/1970 | Zurbrick et al. |
| 3,518,535 A | 6/1970 | Powell |
| 3,519,940 A | 7/1970 | Ludin |
| 3,622,873 A | 11/1971 | Stine et al. |
| 3,628,132 A | 12/1971 | Fussell et al. |
| 3,646,434 A | 2/1972 | Norwich |
| 3,694,742 A | 9/1972 | Bergmanis et al. |
| 3,778,705 A | 12/1973 | Maltby |
| 3,781,672 A | 12/1973 | Maltby et al. |
| 3,826,979 A | 7/1974 | Steinmann |
| 3,862,571 A | 1/1975 | Vogel |
| 3,986,110 A | 10/1976 | Overall et al. |
| 3,991,939 A | 11/1976 | Maclay |
| 4,187,460 A | 2/1980 | Dauge et al. |
| 4,190,201 A | 2/1980 | Geiger |
| 4,194,691 A | 3/1980 | Birnbach et al. |
| 4,228,393 A | 10/1980 | Pile |
| 4,272,718 A | 6/1981 | Kashiuchi et al. |
| 4,332,105 A | 6/1982 | Nir |
| 4,502,288 A | 3/1985 | Lynch |
| 4,517,547 A | 5/1985 | Gray et al. |
| 4,545,396 A | 10/1985 | Miller et al. |
| 4,626,774 A | 12/1986 | Regtien |
| 4,639,831 A | 1/1987 | Iyoda |
| 4,657,039 A | 4/1987 | Bireley et al. |
| 4,675,596 A | 6/1987 | Smith |
| 4,683,904 A | 8/1987 | Iltis |
| 4,795,965 A | 1/1989 | Dooley |
| 4,805,070 A | 2/1989 | Koontz et al. |
| 4,806,848 A | 2/1989 | Demers |
| 4,845,421 A | 7/1989 | Howarth et al. |
| 4,858,063 A | 8/1989 | Laue et al. |
| 5,159,247 A | 10/1992 | Resch |
| 5,210,500 A | 5/1993 | Pingel et al. |
| 5,224,769 A | 7/1993 | Holbrook et al. |
| 5,225,783 A | 7/1993 | Suzuki et al. |
| 5,245,295 A | 9/1993 | Hata et al. |
| 5,301,542 A | 4/1994 | Meitzler et al. |
| 5,311,140 A | 5/1994 | Permuy |
| 5,313,168 A | 5/1994 | Ogawa |
| 5,398,547 A | 3/1995 | Gerardi et al. |
| 5,414,368 A | 5/1995 | Ogawa et al. |
| 5,479,104 A | 12/1995 | Cambell |
| 5,491,423 A | 2/1996 | Turetta |
| 5,537,109 A | 7/1996 | Dowd |
| 5,751,071 A | 5/1998 | Netzer |
| 5,780,718 A | 7/1998 | Weber |
| 5,783,743 A | 7/1998 | Weber |
| 5,844,138 A | 12/1998 | Cota |
| 5,870,302 A | 2/1999 | Oliver |
| 6,239,601 B1 | 5/2001 | Weinstein |
| 6,249,130 B1 | 6/2001 | Greer |
| 6,373,263 B1 | 4/2002 | Netzer |
| 6,575,621 B1 | 6/2003 | Zlochin |
| 6,628,501 B2 | 9/2003 | Toyoda |
| 6,647,782 B2 | 11/2003 | Toyoda |
| 6,756,793 B2 * | 6/2004 | Hirono et al. ............... 324/690 |
| 6,911,829 B2 | 6/2005 | Hilliard et al. |
| 7,049,829 B2 | 5/2006 | Luethi |
| 7,129,713 B2 | 10/2006 | Katz |
| 7,170,302 B2 | 1/2007 | Lee |
| 7,176,700 B2 | 2/2007 | Itakura et al. |
| 7,183,779 B2 | 2/2007 | Hughes |
| 7,267,002 B2 | 9/2007 | Itakura et al. |
| 7,471,093 B2 | 12/2008 | Arisaka |
| 7,834,646 B2 | 11/2010 | Chambon et al. |
| 7,971,482 B2 | 7/2011 | Isogai et al. |
| 8,009,053 B2 | 8/2011 | Veerasamy |
| 2001/0038440 A1 | 11/2001 | Sato |
| 2002/0190284 A1 * | 12/2002 | Murthy et al. ............... 257/286 |
| 2007/0210807 A1 * | 9/2007 | Arisaka .................. 324/664 |
| 2008/0222827 A1 * | 9/2008 | Veerasamy ............ 15/250.12 |

OTHER PUBLICATIONS

D. Wobschall, "A Frequency Shift Dielectric Soil Moisture Sensor", IEEE Transactions on Geoscience Electronics, vol. GE-16, No. 2, Apr. 1978.

D. Wobschall, "Wireless Soil Moisture Sensor Based on Fringing Capacitance", Sensors, 2005, IEEE Mar. 13, 2006. pp. 4, Oct. 30, 2005-Nov. 3, 2005 doi: 10.1109/ICSENS.2005.1597624.

G.Ya. Chernyak, "Dielectric Methods for Investigating Moist Soild", Israel Program for Scientific Translations, Jerusalem 1967, pp. 15-17, 36-40, 65-70.

Sensors Energy and Automation Laboratory, http://www.ee.washington.edu/research/seal/projects/moisture%20, copy printed Jan. 27, 2009.

Wang, Dau-Chung et al., "Application of a Fringe Capacitive Sensor to Small-Distance Measurement" Jpn. J. Appl. Phys., Sep. 2003, vol. 42 Part 1 No. 9A, pp. 5816-5820.

* cited by examiner

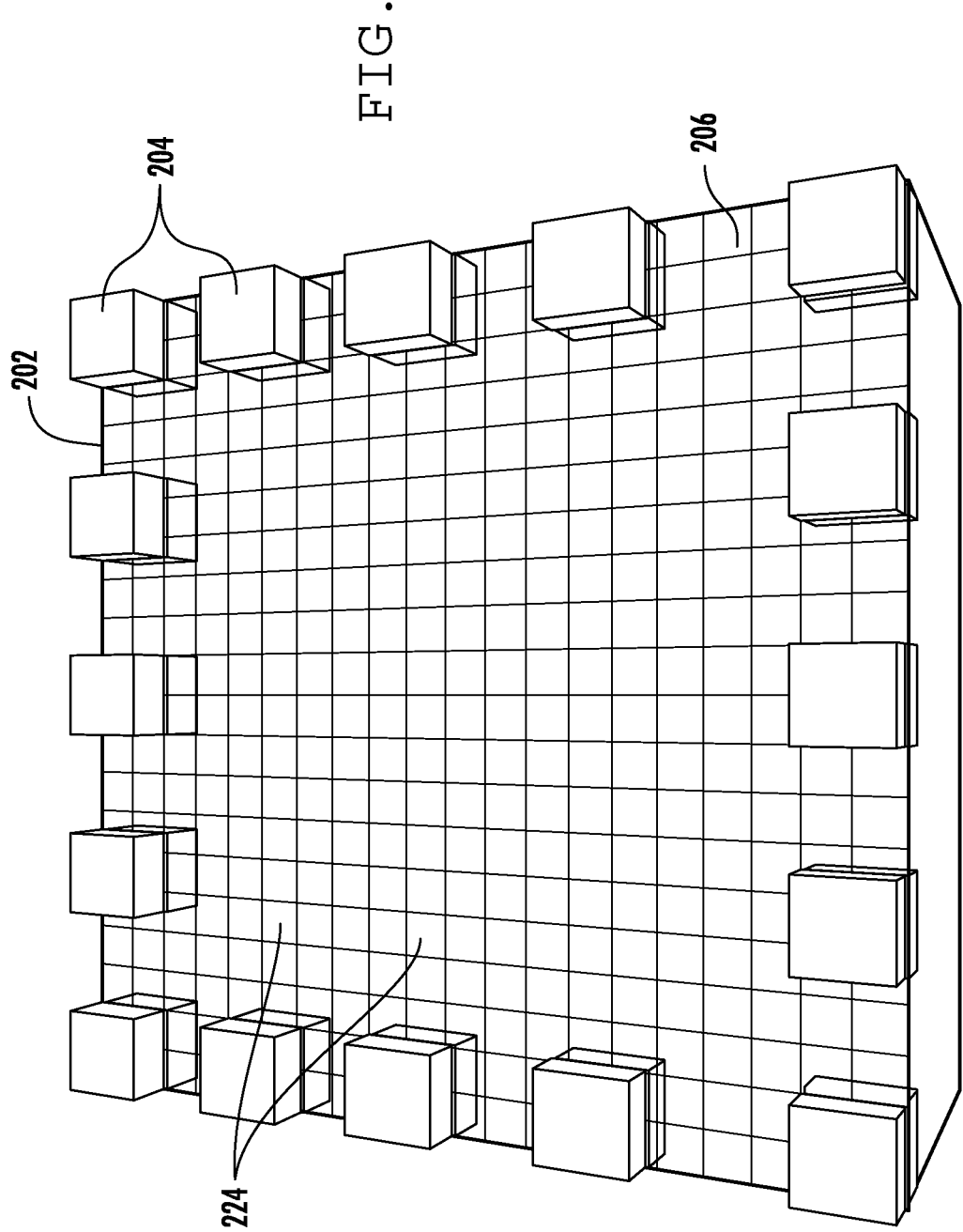

MOISTURE SENSING DEVICES

CROSS-REFERENCE TO RELATED APPLICATIONS

This application is a continuation-in-part application of and claims the benefit of the priority date of U.S. application Ser. No. 13/292,504, filed Nov. 9, 2011, which relies on the disclosure of and the benefit of the priority date of U.S. Provisional Application No. 61/414,657 filed Nov. 17, 2010, each application of which is incorporated herein by reference in its entirety.

BACKGROUND OF THE INVENTION

1. Field of the Invention

The invention relates generally to capacitive moisture sensors. More particularly, embodiments of the invention provide sensing and measurement devices for monitoring mist propagation conditions through the use of electric fields.

2. Description of Related Art

The general concepts surrounding fringing sensor devices have been well documented and have even been discussed in a few patents on fringing sensor devices. For example, U.S. Pat. No. 2,219,497, entitled "Electrostatic Type Test Electrode," shows several embodiments of electrodes which use fringing fields as a sensing technique, which patent is incorporated by reference herein in its entirety. This patent describes devices that are more conductive than capacitive, which is also a characteristic of devices described in U.S. Pat. No. 6,239,601, entitled "Thickness Measurement Device for Ice, or Ice Mixed with Water or Other Liquid," as well as in U.S. Pat. No. 4,639,831, and Great Britain Patent No. 2149922 entitled "Capacitive Moisture Sensor and Process for Producing Same."

Other sensors, moisture monitoring systems, and electrical circuits instructive as to embodiments of systems, devices, and methods of the invention include for example any of U.S. Pat. Nos. 2,043,241, 2,076,441, 2,121,103, 2,207,906, 2,219,497, 2,285,152, 2,357,984, 2,373,846, 2,570,218, 2,455,450, 2,508,081, 2,570,218, 2,611,021, 2,662,408, 2,729,786, 2,817,234, 2,849,882, 2,969,186, 3,046,479, 3,079,089, 3,112,647, 3,129,415, 3,177,427, 3,218,551, 3,231,815, 3,278,843, 3,443,213, 3,515,987, 3,518,535, 3,519,940, 3,622,873, 3,628,132, 3,646,434, 3,694,742, 3,778,705, 3,781,672, 3,826,979, 3,862,571, 3,986,110, 3,991,939, 4,187,460, 4,190,201, 4,194,691, 4,228,393, 4,272,718, 4,332,105, 4,502,288, 4,517,547, 4,545,396, 4,626,774, 4,639,831, 4,657,039, 4,675,596, 4,683,904, 4,795,965, 4,805,070, 4,806,848, 4,845,421, 4,858,063, 5,159,247, 5,210,500, 5,224,769, 5,225,783, 5,245,295, 5,301,542, 5,311,140, 5,313,168, 5,398,547, 5,414,368, 5,479,104, 5,491,423, 5,537,109, 5,751,071, 5,780,718, 5,783,743, 5,844,138, 5,870,302, 6,249,130, 6,373,263, 6,552,552, 6,575,621, 6,628,501, 6,647,782, 6,756,793, 6,911,829, 7,049,829, 7,129,713, 7,170,302, 7,176,700, 7,183,779, 7,267,002, 7,471,093, 7,834,646, 7,971,482, and 8,009,053, as well as U.S. Published Patent Application No. 2001/038,440, which patents and publication are each incorporated by reference herein in their entireties.

It has been found by experimentation that fringing capacitors with the sensor's metal runs in direct contact with the cover plate of this sort are 73 times more conductive than they are capacitive. Moisture ions pass directly through the cover plate to the runs and short them out making them insensitive to capacitive changes due to the moisture found on top of the glass. An air gap, as described in this invention, acts to insulate the runs from the moisture and prevent them from shorting out. Note that the capacitive change in a sensor such as this is approximately 60 pico-farads from dry to fully wet and this is swamped out by the conductivity which can be as small as 228 mega-ohms but which is 73 times more conductive than capacitive.

SUMMARY OF THE INVENTION

The fringing capacitor moisture sensor 170 seen in FIGS. 1A-B comprises two intertwined or interlocking runs that are not connected to each other. An AC signal applied to the two interlocking runs creates a fringing field both above and below the runs. Above the runs this field penetrates an evaporative membrane 206 and the moisture 220 acts as a dielectric changing the electrical value of the capacitance of the sensor and can be seen by electrical circuits connected to the capacitor. Thus the amount of moisture 220 seen on the evaporative membrane 206 can be directly translated to a voltage or current which can then be read by a computer to control misting or other moisture features.

Another embodiment of the invention provides a mesh cell capacitive moisture sensor 218 as seen in FIG. 2. This mesh cell sensor comprises an external wire mesh electrode 202 above the moisture 220 resting on the evaporative membrane 206. Below the evaporative membrane 206 is a hermetically sealed enclosure that contains dry electrode 212. An AC field is applied between the wet electrode 202 and the dry electrode 212. This creates an electric field between the two capacitor plates. Dispersed within that electric field are water droplets 220. The water droplets 220 act as a dielectric modifying the capacitance of the mesh cell capacitor 218. With the proper electrical circuitry the amount of moisture can be converted to an electric voltage or current which can be processed by a computer and used to modulate the misting of plants in the vicinity.

An object of this invention is to introduce an air gap either between the runs of the fringing sensor and the evaporative membrane, or between the wet and dry electrodes in the mesh cell type sensor. A further object of the invention is a low heat mass evaporative membrane that will allow moisture to evaporate at a rate more closely with that of a leaf.

Specific objects of the invention include a fringing capacitor sensor for detecting moisture comprising: a printed circuit board (PCB) comprising first and second conductive electrodes; an evaporative membrane disposed above the PCB; a box supporting the PCB and the evaporative membrane, which box comprises a hermetically sealed volume disposed between the evaporative membrane and the bottom of the box.

Such fringing capacitors can have first and second electrodes each forming a pattern comprising parallel, perpendicular, or circular traces, or a combination thereof, wherein the patterns are symmetrical.

The fringing capacitor sensors can comprise an evaporative membrane that is coated with a hydrophilic material.

Alternatively or in addition, the fringing capacitor sensors can have the PCB, the electrodes, the evaporative membrane, or the box bottom, or a combination thereof, configured to be light absorbing to heat the hermetically sealed volume when exposed to light. For example, such fringing capacitor sensors can have a surface of the evaporative membrane painted black to absorb light.

Further provided is a mesh cell sensor for detecting moisture comprising: a first wet conductive electrode comprising a wire mesh array; a second dry conductive electrode disposed on a non-conductive support; an evaporative membrane disposed between the first and second electrodes; a box supporting the first and second electrodes and the evaporative membrane in a manner that provides for a hermetically sealed volume disposed between the evaporative membrane and the bottom of the box.

Such mesh cell sensors can have an evaporative membrane coated with a hydrophilic material.

Further, the mesh cell sensors can be configured such that the non-conductive support, the evaporative membrane, or the box bottom, or a combination thereof, are light absorbing to heat the hermetically sealed volume when exposed to light. One way to make these structures light absorbing is to paint a surface black, such as painting a surface of the evaporative membrane black to absorb light.

BRIEF DESCRIPTION OF THE DRAWINGS

The accompanying drawings illustrate certain aspects of some embodiments of the present invention, and should not be used to limit or define the invention. Together with the written description the drawings serve to explain certain principles of the invention.

FIGS. 3A, 3B, 3C, and 3D are schematic diagrams showing perspective views, respectively, of a mesh cell moisture sensor of the invention.

DETAILED DESCRIPTION OF VARIOUS EMBODIMENTS OF THE INVENTION

Reference will now be made in detail to various exemplary embodiments of the invention. It is to be understood that the following discussion of exemplary embodiments is not intended as a limitation on the invention. Rather, the following discussion is provided to give the reader a more detailed understanding of certain aspects and features of the invention.

Figure 1A:
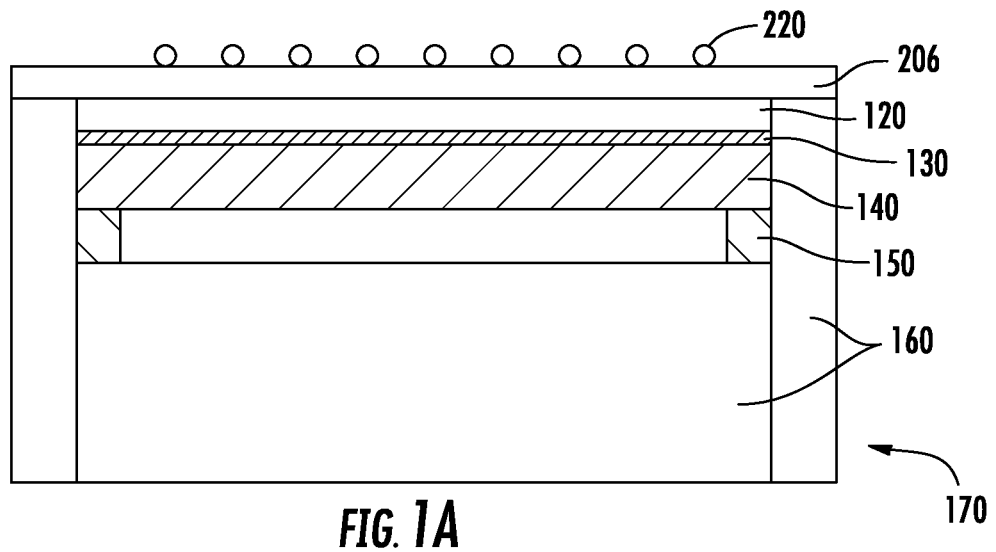
FIGS. 1A and 1B are schematic diagrams showing side and top views, respectively, of a fringing moisture sensor of the invention.
Figure 1B:
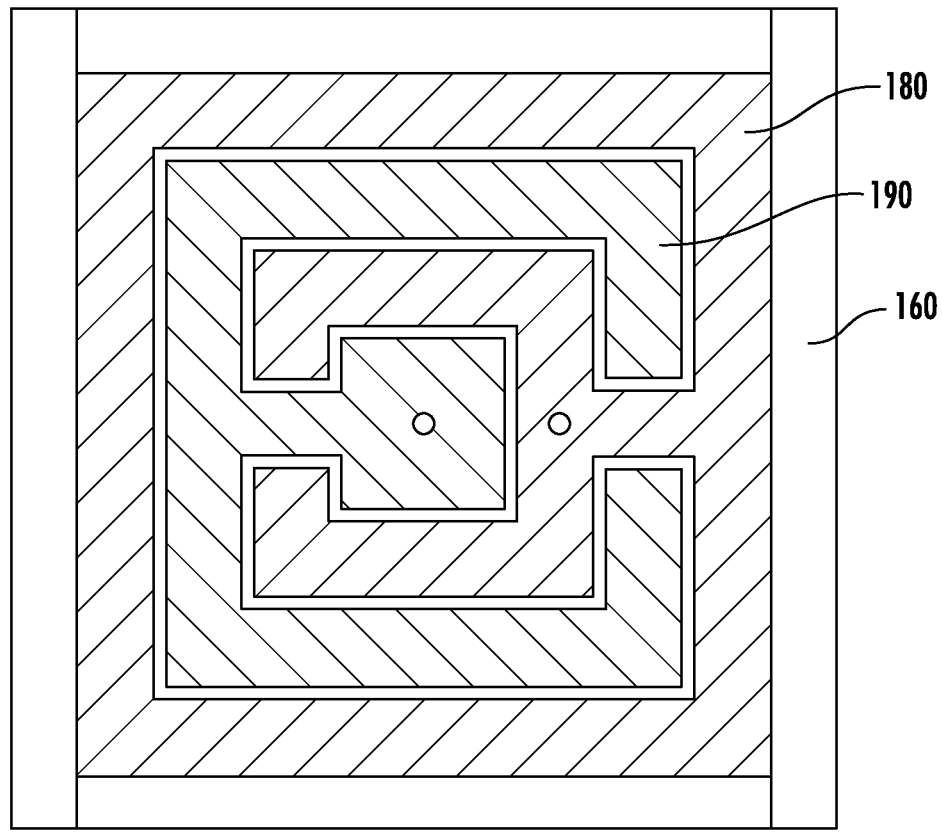
Figure 2:
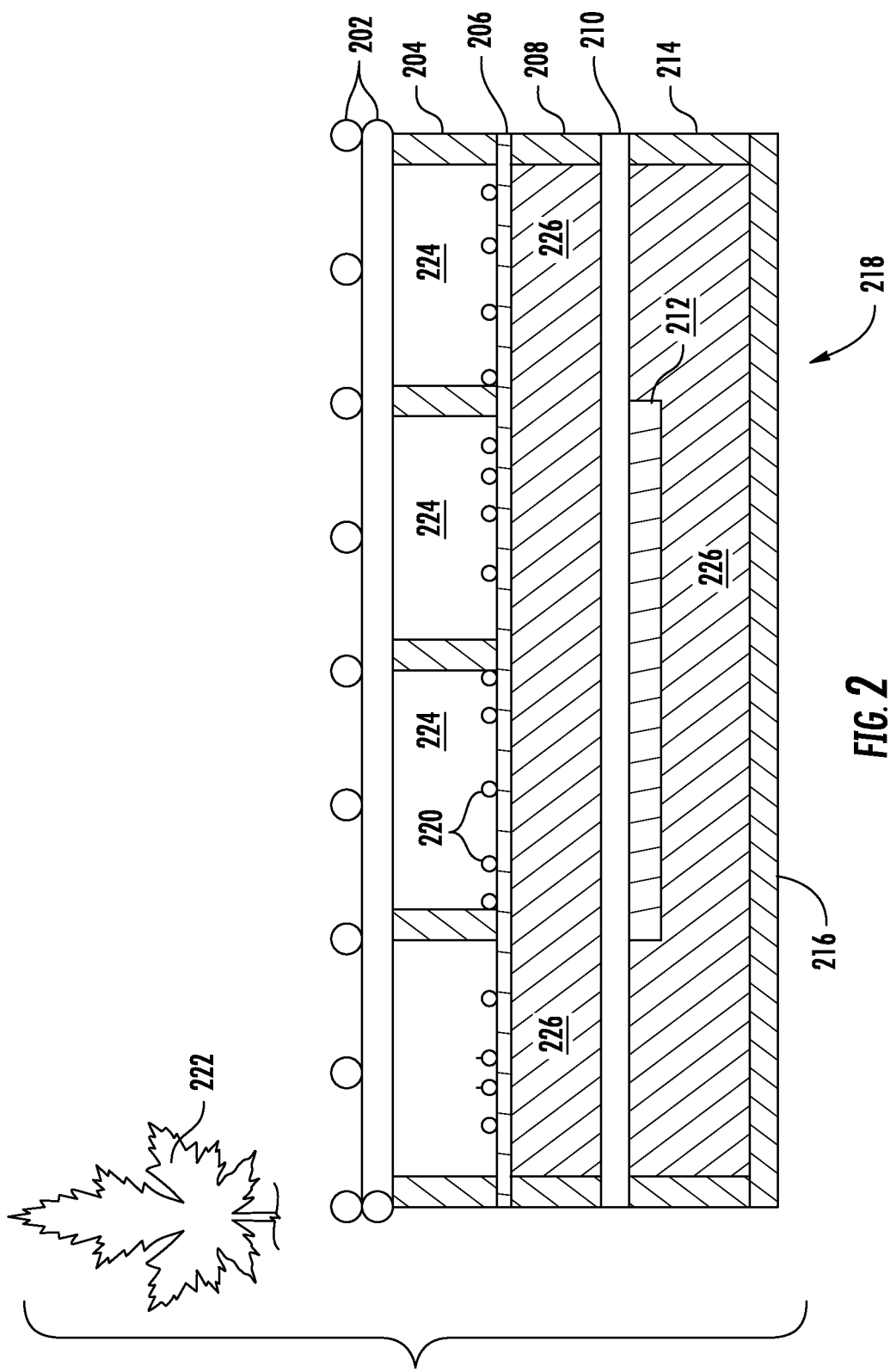
FIG. 2 is a schematic diagram showing a side view of a mesh cell moisture sensor of the invention.
Figure 3B:
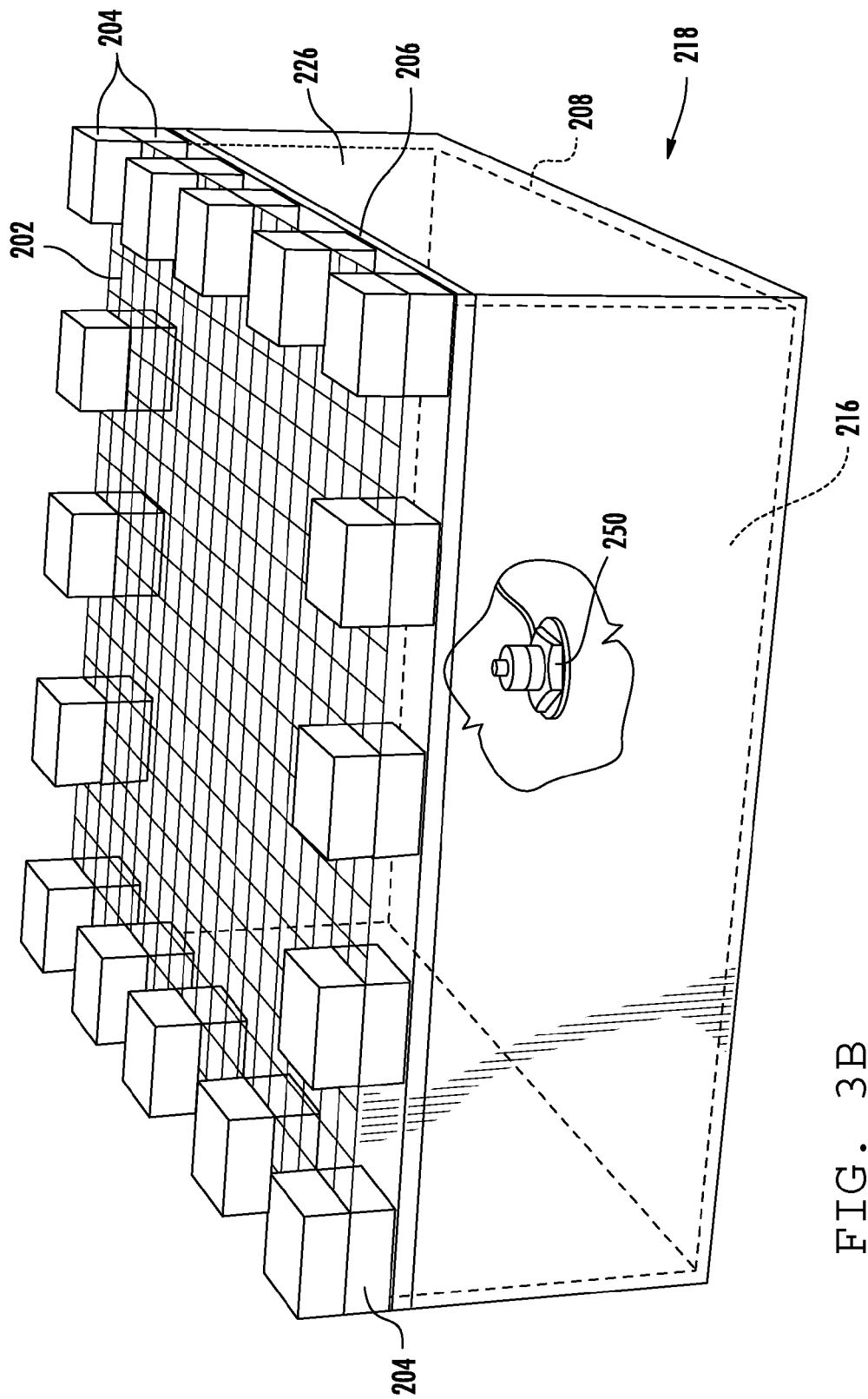
Figure 3C:
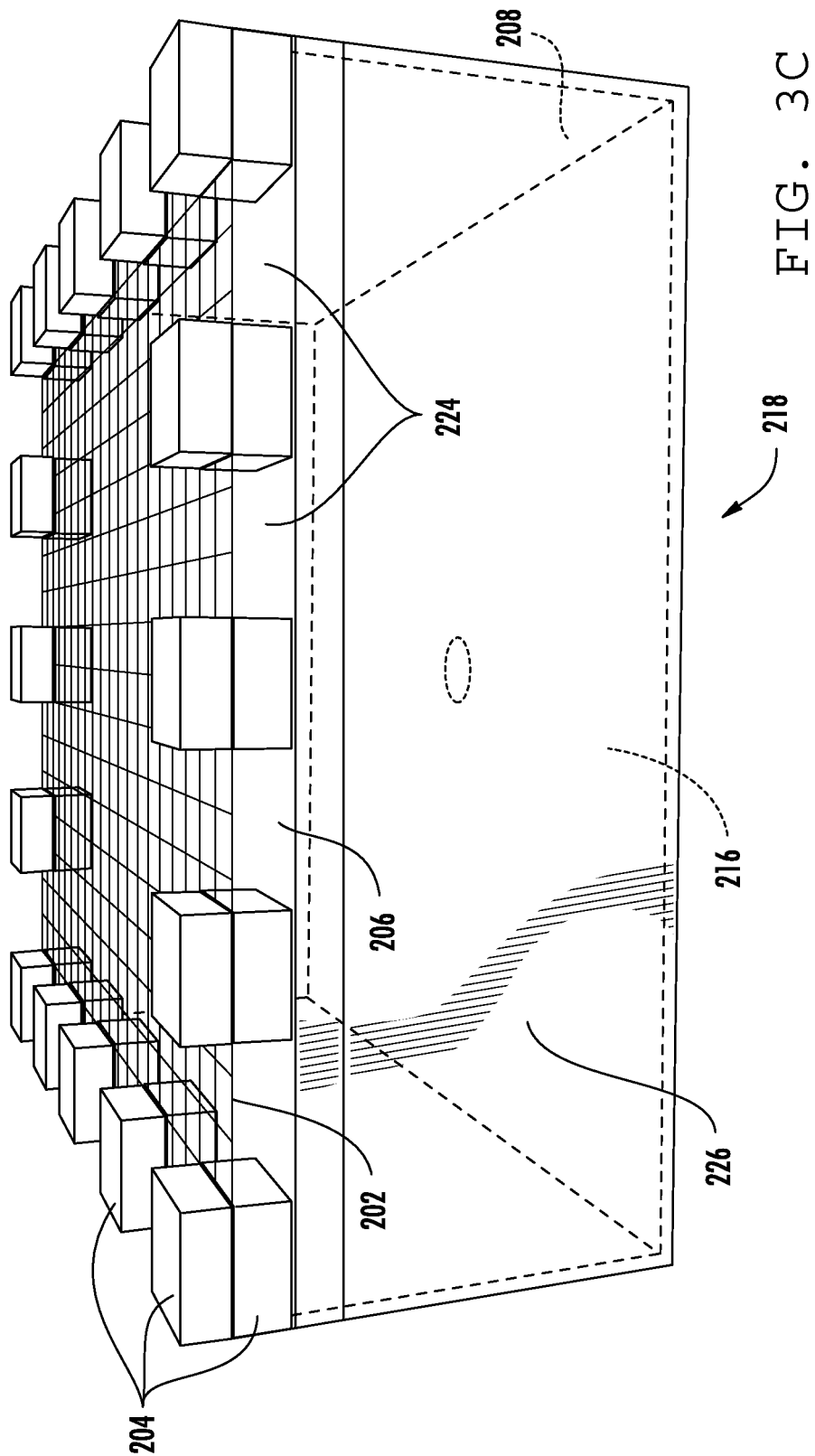
Figure 3D:
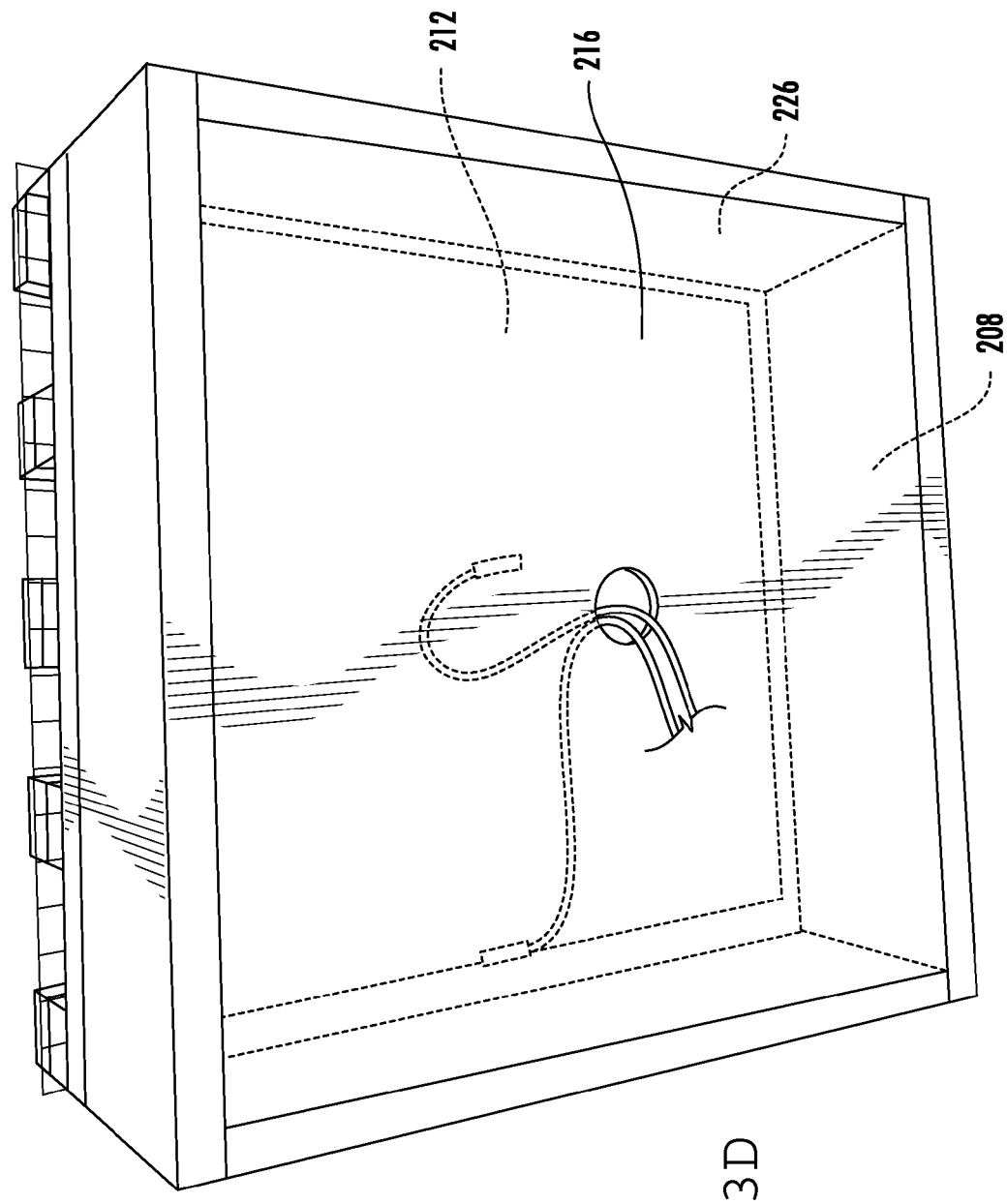

Referring now to the drawings and more particularly to FIGS. 1A-B, one embodiment of the fringing capacitor moisture sensor of the present invention is shown and referenced generally as sensor 170. Sensor 170 comprises a first capacitor electrode 180 and a second capacitor electrode 190 intertwined but not connected. During use of the sensor, an AC voltage is applied to the two electrodes and a fringing electric field exists above and below the two electrodes. When moisture 220 is disposed on top of the evaporative membrane 206, this moisture acts as a dielectric to the fringing capacitive sensor 170 enabling the moisture 220 to be sensed using an electrical circuit detector.

The top of the sensor where the moisture gathers is a smooth glass, ceramic, plastic or other non conductive substance with a dielectric constant that remains the same with temperature variations that allows any mineral buildup to wash off and is easily kept clean by a quick wipe off of the surface. Also, since the moisture acts as a dielectric for the capacitive sensor, any mineral buildup is not sensed as much as the water since the dielectric constant of water eighty-eight (88) is so much greater than the dielectric constant of the minerals (2 to 4). In embodiments of the invention, the sensing fringing capacitor comprises a small air gap between the dry part of the evaporative membrane and the electrical pathways that generate the electric field. A gap of air, or inert gas, is provided above each capacitive moisture sensor; this air gap may be very small allowing the sensor and cover to touch but not adhere to one another. The void or spacing in such a configuration allows for isolation of the electrical pathways from the non-conductive evaporative membrane, which aids in the prevention of the metal plates from becoming conductive to each other.

Looking at the side view, FIG. 1A, the device 170 first comprises a non-conductive evaporative membrane 206 of thin material that can have a low heat mass to the moisture 220 falling on top of it. In one embodiment, the evaporative membrane 206 is coated on the bottom (the face of the evaporative membrane 206 that faces the top of the fringing sensor runs 180 and 190) to aid evaporative membrane 206 in absorbing sunlight thus heating the evaporative membrane 206 and aiding it in evaporation due to heat. For example, a dark paint or plastic coating could be used to coat the back of the evaporative membrane 206 to absorb sunlight and convert it to heat. Alternatively, or in addition, the evaporative membrane 206 could be transparent/clear and the sensor (180, 190) could be made out of a dark material or painted a dark color below the membrane 206 to absorb sunlight. These configurations result in a greenhouse effect which is used to heat the evaporative membrane 206 to aid in evaporation of the water droplets. Alternatively, or in addition, a source of heat internal to the hermetically sealed box could also be used to heat the evaporative membrane 206 to aid in evaporation. The top of the evaporative membrane 206 could be coated in a hydrophilic coating. This coating would have a high surface tension and allow water droplets to spread out exposing more area of the water to the atmosphere thus causing it to evaporate faster.

Figure 4A:
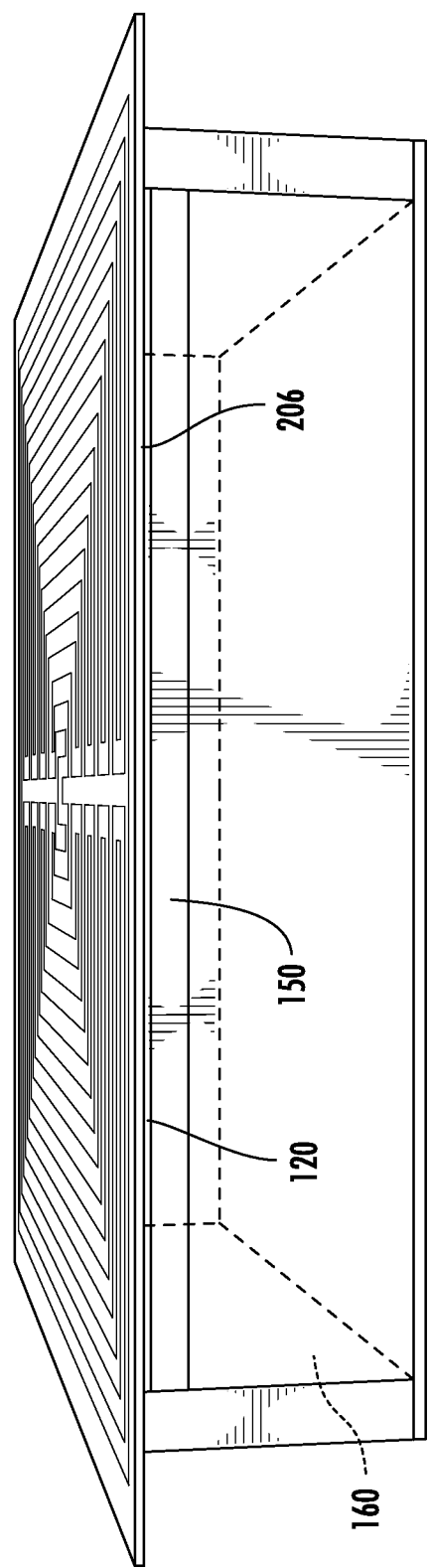
FIGS. 4A, 4B, and 4C are schematic diagrams showing perspective views, respectively, of a fringing moisture sensor of the invention.
Figure 4B:
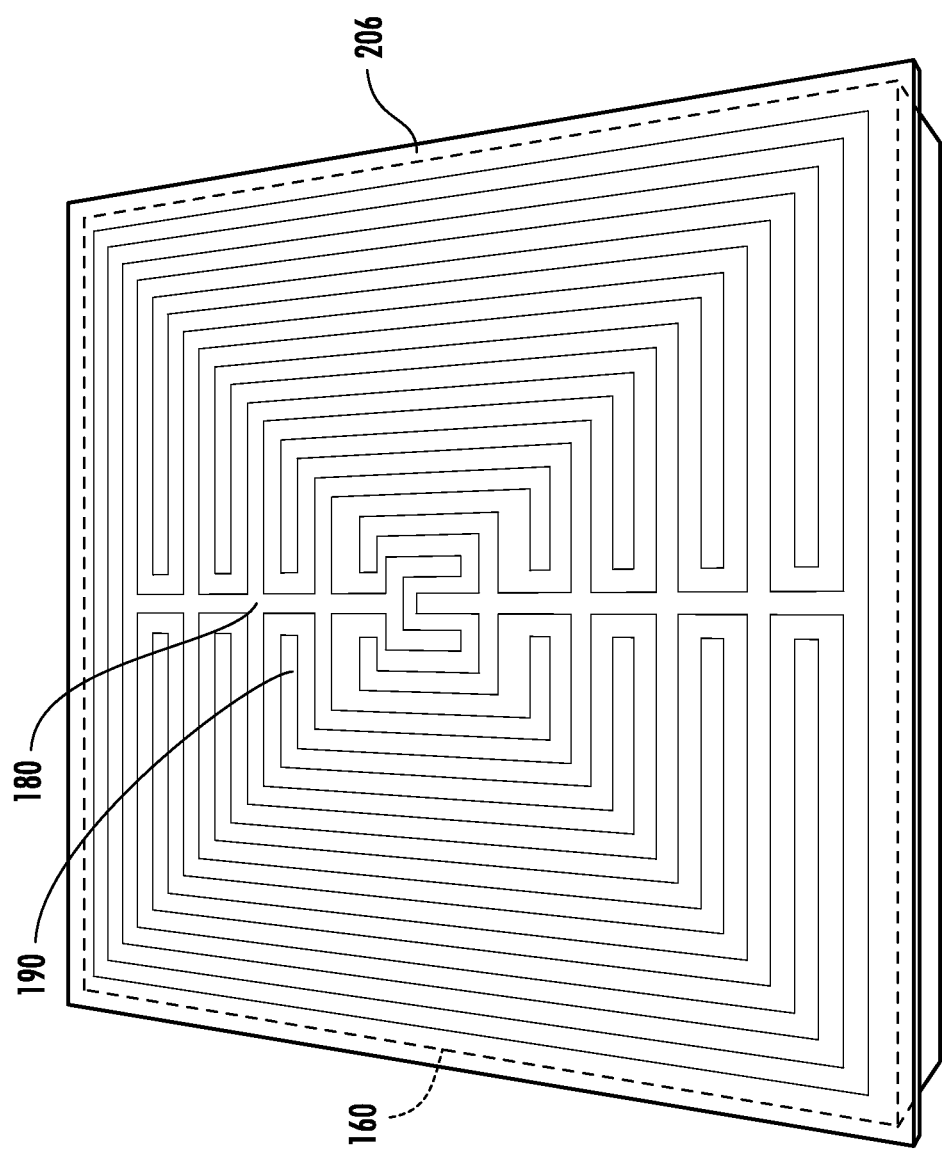
Figure 4C:
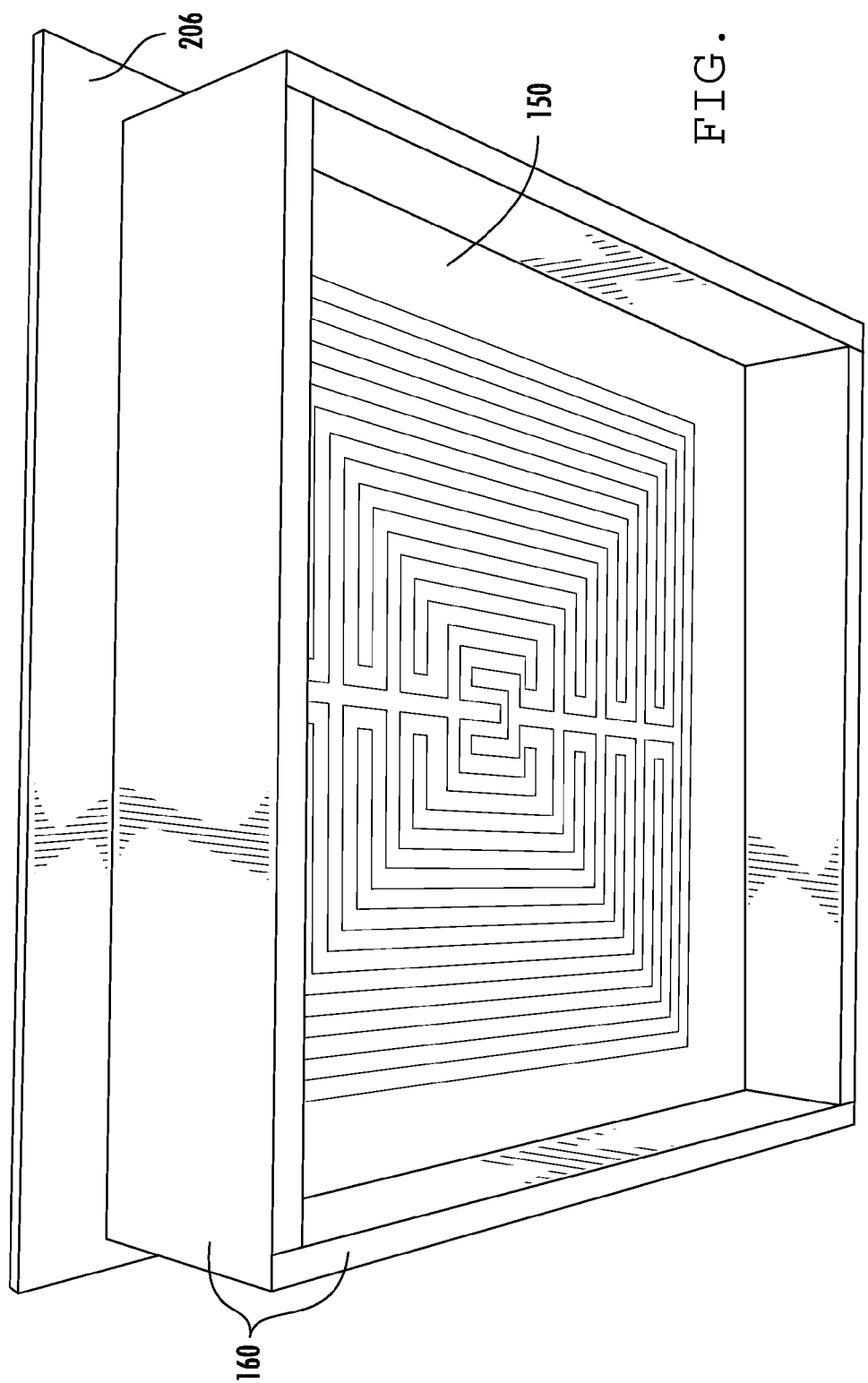

This membrane 206 is supported by the non-conductive box sides 160. Below the evaporative membrane 206 is a void area 120 to provide insulation between the non-conductive membrane 206 and the metal runs 130 of the printed circuit board fringing sensor electrodes 180 and 190. The metal electrodes 130 are supported by the printed circuit board (PCB) material 140 which in turn is supported by the non-conductive supports 150. The void area 120 is hermetically sealed by the evaporative membrane 206 and the printed circuit board 140 to prevent moisture 220 from entering the void area 120. The internal area below the printed circuit board 140 is also hermetically sealed to prevent moisture 220 from entering the back surface of the printed circuit board 140. FIG. 4A is a perspective view of the fringing capacitor moisture sensor 170.

FIGS. 2, 3A-D are schematic diagrams of a mesh cell sensor 218 of the invention. In one embodiment, the sensor comprises a wet electrode 202 usually comprising a wire mesh. The wet electrode 202 is supported by plastic supports 204 (or any non-conductive non-water absorbing material) to provide the mesh in a suspended state above an evaporative membrane 206. This configuration provides for void areas 224 between the mesh 202 and the membrane 206, which void areas during use of the device allow moisture 220 to escape and not fill the void cell areas 224. The wet electrode 202 and wet cell void areas 224 are open to the outside environment to allow moisture 220 to enter as well as air and sunlight to aid in the evaporation process. Below the plastic supports 204 is an evaporative membrane 206 which comprises a thin non-conductive material with very low heat mass to enable it to match the evaporation rate of the surrounding leaves 222. In one embodiment, the bottom of evaporative membrane 206 is painted with a dark color to absorb sunlight to aid in the evaporative process. The evaporative membrane 206 could also be clear and the dry electrode 212 could be painted (or comprise a material) with a dark color to absorb sunlight and generate heat to aid the evaporative membrane 206 in evaporation. A source of heat internal to a hermetically sealed box could also be used to heat the evaporative membrane 206 to aid in evaporation. This evaporative membrane 206 could also be coated with a hydrophilic coating to cause the water droplets 220 to spread out and evaporate faster. Below the evaporative membrane is a hermetically sealed box 226 with a void area inside. The box 226 is formed from the evaporative membrane 206, the box sides 208, 214 and the box bottom 216.

Within the box 226 is a connector 250. Connector 250 is operably connected with each electrode by a wire lead. Connector 250 is then connected by wire leads to a detector. Connector 250 can be of the BNC or F type or it can be two parallel connections. For BNC or F connector the shield would be connected to the mesh wet electrode 202. A system for monitoring moisture levels may comprise one or more and preferably a plurality of sensors 218 in operable communication with detection circuitry in operable communication with a controller, software, and a computer for processing the electrical signals obtained from the sensor into information indicative of whether more or less moisture is needed for a particular application. The computer can comprise a processor for implementing the software and determining moisture levels on the sensor. A representative moisture sending system or moisture management system of the invention can comprise a software program, in combination with computer hardware, and one or more sensors 218, wherein the system comprises: a processor embedded on a computer or logic device for determining a dry value or starting value of the sensor, then determining a sensing capacitor value of the sensing capacitor when wet, then determining a change in sensor capacitance by analyzing the sensing capacitor value in relation to the dry value or starting value of the sensing capacitor and optionally instructing a misting system in operable communication with the computer to activate or deactivate misting based on the change in sensor capacitance.

In embodiments, the Sensor 218 comprises non-conductive materials except for the wet electrode 202 and the dry electrode 212 and corresponding electrical leads and connectors for transporting the electrical current to a detector. The dry electrode 212 is supported by the dry electrode carrier 210 just below the evaporative membrane 206. The wet electrode 202 and the dry electrode 212 are conductive and connected to an AC source usually with the wet electrode 202 connected to ground. An electric field exists between the wet electrode 202 and the dry electrode 212 with the moisture droplets 220 being within the electric field. The moisture droplets 220 add dielectric to the capacitor formed by the wet electrode 202 and the dry electrode 212. This added dielectric increases the mesh cell sensor capacitance which can then be incorporated into an electric circuit to convert the amount of moisture 220 to a voltage or current or modify an oscillator's frequency.

The advantages of the invention are numerous. For FIGS. 1A-B only the top side of the evaporative membrane 206 is exposed to moisture 220 thus any build up of dirt or calcium from the water can be easily washed off and cleaned with a soft cloth. An air gap (otherwise referred to as a void area) between the evaporative membrane 206 and the fringing sensor runs 180, 190 prevents the runs 180, 190 from contacting the bottom of the evaporative membrane 206 and thus shorting out the very sensitive electronics needed to detect the moisture on top of the evaporative membrane 206. The evaporative membrane 206 moisture absorption capability is small compared to the amount of moisture 220 on top of the evaporative membrane 206 thus not affecting the amount of moisture 220 sensed by the fringing capacitor runs 180, 190. The heat mass of the evaporative membrane 206 is low as it is made of thin material. In one embodiment, the material is approximately 0.03 of an inch thick. A general range of thicknesses could be used, but preferably 0.03 inches or less. In preferred embodiments, the back of the evaporative membrane 206 is painted black to absorb sunlight or the dry electrode (FIG. 2 component 212) or sensor runs (FIG. 1B components 180 and 190) can be painted with a dark color to absorb sunlight through the clear evaporative membrane 206 to use the greenhouse effect to aid the membrane 206 in gaining heat to cause the moisture 220 to evaporate quickly. A heat source could be included in the hermetically sealed box to heat the evaporative membrane 206 to cause it to evaporate the moisture at a faster rate than solar heating would allow for.

To demonstrate how the sensors can be used, a method of detecting moisture levels in the environment is included within the scope of the invention. The AC current and voltage applied to the fringing runs 180, 190 or to the wire mesh 202 and the dry electrode 212 form an electric field that exists above the fringing sensor 180, 190 or between the wet electrode 202 and the dry electrode 212. Moisture within this field acts as a dielectric and alters the capacitance of the sensor. The more moisture, the higher the dielectric and the larger the capacitance of the sensor. The AC signal is usually generated by an oscillator with frequencies between $10^7$ and $10^8$ Hz, as those frequencies most affect change and oscillation of the water dipole.

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Other embodiments of the invention will be apparent to those skilled in the art from consideration of the specification and practice of the invention. Where a range of values is provided in this specification, each value between the upper and lower limits of that range is also specifically disclosed. The upper and lower limits of these smaller ranges may independently be included or excluded in the range as well. As used in this specification, the singular forms "a," "an," and "the" include plural referents unless the context clearly dictates otherwise. It is intended that the specification and examples be considered as exemplary in nature and that variations that do not depart from the essence of the invention are intended to be within the scope of the invention. Further, each reference cited in this disclosure is hereby incorporated by reference herein in its entirety.

The invention claimed is:

1. A fringing capacitor sensor for detecting moisture comprising:
    a printed circuit board (PCB) comprising first and second conductive electrodes;
    an evaporative membrane disposed above the PCB;
    a void area of an inert gas in direct contact with the electrodes and disposed between the evaporative membrane and the electrodes; and
    a box supporting the PCB and the evaporative membrane, which box comprises a hermetically sealed volume disposed between the PCB and the evaporative membrane.
2. The fringing capacitor sensor of claim 1, wherein the first and second electrodes each form a pattern comprising parallel, perpendicular, or circular traces, or a combination thereof, wherein the patterns are symmetrical.

3. The fringing capacitor sensor of claim 1, wherein the PCB, the electrodes, the evaporative membrane, or the box bottom, or a combination thereof heat the hermetically sealed volume when exposed to light.

4. The fringing capacitor sensor of claim 3, wherein a surface of the evaporative membrane is painted black to absorb light.

5. A mesh cell sensor for detecting moisture comprising:
    a first conductive electrode comprising a wire mesh array;
    a second conductive electrode disposed on a non-conductive support;
    an evaporative membrane disposed between the first and second electrodes;
    a void area of an inert gas disposed between the evaporative membrane and the second electrode; and
    side supports for supporting the evaporative membrane.

6. The mesh cell sensor of claim 5, wherein a surface of the evaporative membrane is painted black to absorb light.

\* \* \* \* \*